United States Patent
Geier

(10) Patent No.: US 9,993,312 B2
(45) Date of Patent: Jun. 12, 2018

(54) INTRAORAL REFERENCE BODY

(71) Applicant: Zfx GmbH, Dachau (DE)

(72) Inventor: Andreas Geier, Gargazon (IT)

(73) Assignee: Zfx GmbH, Dachau (DE)

( * ) Notice: Subject to any disclaimer, the term of this patent is extended or adjusted under 35 U.S.C. 154(b) by 0 days. days.

(21) Appl. No.: 14/914,874

(22) PCT Filed: Jan. 13, 2014

(86) PCT No.: PCT/EP2014/050476
§ 371 (c)(1),
(2) Date: Feb. 26, 2016

(87) PCT Pub. No.: WO2015/028157
PCT Pub. Date: Mar. 5, 2015

(65) Prior Publication Data
US 2016/0213442 A1    Jul. 28, 2016

(30) Foreign Application Priority Data

Aug. 30, 2013    (EP) .................................... 13182321

(51) Int. Cl.
*A61C 1/00*    (2006.01)
*A61B 90/00*    (2016.01)
(Continued)

(52) U.S. Cl.
CPC .............. *A61B 90/39* (2016.02); *A61B 6/145* (2013.01); *A61B 6/583* (2013.01); *A61C 8/0001* (2013.01);
(Continued)

(58) Field of Classification Search
CPC ......... A61B 90/39; A61B 6/145; A61B 6/583; A61B 2090/3937; A61B 5/0088;
(Continued)

(56) References Cited

U.S. PATENT DOCUMENTS

D296,714 S    7/1988  Averill et al.
D317,200 S    5/1991  Jorneus
(Continued)

FOREIGN PATENT DOCUMENTS

DE    10000058 A1    7/2001
DE    10019331 B4    10/2001
(Continued)

OTHER PUBLICATIONS

"U.S. Appl. No. 29/465,669, Non Final Office Action dated Oct. 15, 2014", 9 pgs.
(Continued)

*Primary Examiner* — Cris L Rodriguez
*Assistant Examiner* — Mirayda A Aponte
(74) *Attorney, Agent, or Firm* — Schwegman Lundberg & Woessner, P.A.

(57) ABSTRACT

The present application relates to reference body for intraoral scan procedures adapted to be releasably mountable to a dental implant. The reference body comprises a cylindrical body portion extending along a longitudinal axis from an apical end to a coronal end, the apical end abutting the dental implant in a mounted state of the reference body, a coronal end surface defining the coronal end of the reference body, a first radial protrusion protruding from the body portion in a first radial direction, and a second radial protrusion protruding from the body portion in a second radial direction. The first radial protrusion and the second radial protrusion have different cross-sectional shapes in a cross-section perpendicular to the longitudinal axis of the reference body.

19 Claims, 5 Drawing Sheets

Figure 5:
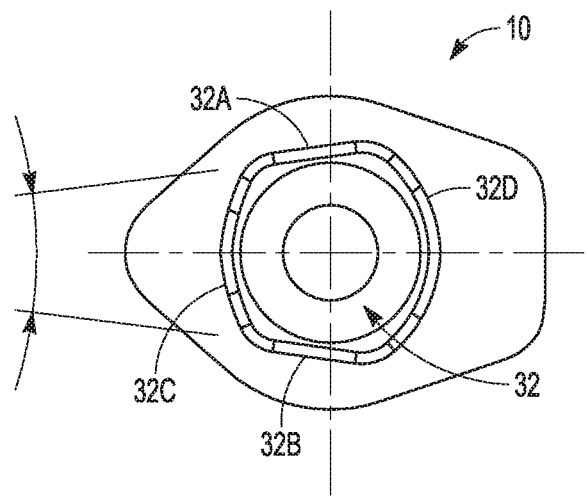

(51) Int. Cl.
*A61B 6/14* (2006.01)
*A61B 6/00* (2006.01)
*A61C 9/00* (2006.01)
*A61C 8/00* (2006.01)
*A61B 5/00* (2006.01)
*A61B 5/107* (2006.01)

(52) U.S. Cl.
CPC .......... *A61C 9/0053* (2013.01); *A61B 5/0088* (2013.01); *A61B 5/1079* (2013.01); *A61B 2090/3937* (2016.02)

(58) Field of Classification Search
CPC ....... A61B 5/1079; A61B 1/24; A61C 8/0001; A61C 9/0053; A61C 8/006; A61C 8/0074; A61C 8/0012
USPC ..... 433/29, 72, 75, 172–173, 181–182, 220; 382/128
See application file for complete search history.

(56) References Cited

U.S. PATENT DOCUMENTS

| | | | |
|---|---|---|---|
| 5,857,853 | A | 1/1999 | Van Nifterick et al. |
| 6,126,445 | A | 10/2000 | Willoughby |
| 6,283,753 | B1 | 9/2001 | Willoughby |
| D469,535 | S | 1/2003 | Lidskog et al. |
| 7,059,856 | B2 | 6/2006 | Marotta |
| 7,314,374 | B2 | 1/2008 | Angthun et al. |
| 7,599,468 | B2 | 10/2009 | Zuendorf et al. |
| 7,731,497 | B2 | 6/2010 | De Moyer |
| 8,275,184 | B2 | 9/2012 | Schneider et al. |
| D676,965 | S | 2/2013 | Sibhatu et al. |
| D688,799 | S | 8/2013 | Steinbrecher |
| 8,801,435 | B2 | 8/2014 | Jahn |
| 2005/0019728 | A1 | 1/2005 | Rostagno et al. |
| 2008/0176188 | A1 | 7/2008 | Holzner et al. |
| 2011/0045431 | A1 | 2/2011 | Groscurth et al. |
| 2011/0294093 | A1 | 12/2011 | Herweg et al. |
| 2012/0135371 | A1* | 5/2012 | Jahn .................. A61C 9/0053 433/72 |
| 2012/0237899 | A1 | 9/2012 | Holmstrom et al. |
| 2012/0251974 | A1 | 10/2012 | Katz |
| 2012/0251978 | A1 | 10/2012 | Katz |
| 2012/0300908 | A1 | 11/2012 | Mayer |
| 2013/0004919 | A1 | 1/2013 | Kirchner et al. |
| 2013/0302752 | A1 | 11/2013 | Schneider |
| 2014/0295374 | A1* | 10/2014 | Jo .................. A61C 8/0022 433/147 |
| 2015/0209122 | A1* | 7/2015 | Piasini ............. A61C 8/0001 433/196 |

FOREIGN PATENT DOCUMENTS

| | | |
|---|---|---|
| DE | Des. 000267471-0008 | 2/2005 |
| DE | Des. 000623749-0001 | 12/2006 |
| DE | 102006052419 A1 | 5/2008 |
| DE | Des. 40403106-0001 | 8/2009 |
| DE | Des. 40403106-0002 | 8/2009 |
| DE | Des. 40403106-0003 | 8/2009 |
| DE | Des. 40403106-0005 | 8/2009 |
| DE | Des. 40403107-0001 | 8/2009 |
| DE | Des. 40403107-0003 | 8/2009 |
| DE | Des. 001201370-0001 | 4/2010 |
| DE | Des. 001201370-0002 | 4/2010 |
| DE | Des. 001757188-0001 | 9/2010 |
| DE | 102009014013 A1 | 10/2010 |
| DE | Des. 001247639-0001 | 12/2010 |
| DE | Des. 402010006793-03 | 2/2011 |
| DE | 202010017228 U1 | 5/2011 |
| DE | 102010021601 A1 | 12/2011 |
| DE | 10201114664 A1 | 3/2012 |
| DE | Des. 40203557-0001 | 4/2012 |
| DE | 102010062105 A1 | 5/2012 |
| DE | Des. 40203557-0002 | 5/2012 |
| DE | Des. 40203557-0005 | 5/2012 |
| DE | Des. 40203557-0006 | 5/2012 |
| DE | Des. 40203557-0007 | 5/2012 |
| DE | Des. 40203557-0008 | 5/2012 |
| DE | Des. 40203557-0009 | 5/2012 |
| DE | Des. 40203557-0010 | 5/2012 |
| DE | 102011003561 A1 | 8/2012 |
| DE | Des. 40203557-0003 | 11/2012 |
| DE | Des. 40203557-0004 | 11/2012 |
| DE | Des. 001353189-0009 | 12/2012 |
| DE | Des. 001355044-0001 | 1/2013 |
| DE | Des. 001355044-0002 | 1/2013 |
| DE | 10201105336 A1 | 3/2013 |
| EP | 0960604 A1 | 12/1999 |
| EP | 0867153 B1 | 2/2003 |
| EP | 1310217 B1 | 10/2008 |
| EP | 1848366 B1 | 10/2008 |
| EP | 2130514 A1 | 12/2009 |
| EP | 2218423 B1 | 5/2012 |
| EP | 2457536 A2 | 5/2012 |
| EP | 2462893 A1 | 6/2012 |
| EP | 2494938 A1 | 9/2012 |
| KR | 10-2012-0057540 A | 6/2012 |
| KR | 10-1199203 B1 | 11/2012 |
| KR | 10-2012-0136858 A | 12/2012 |
| WO | WO-9625120 A1 | 8/1996 |
| WO | WO-03100729 A1 | 12/2003 |
| WO | WO-2004085956 A2 | 10/2004 |
| WO | WO-2006045965 A1 | 5/2006 |
| WO | WO-2007050436 A2 | 5/2007 |
| WO | WO-2008045965 A2 | 4/2008 |
| WO | WO-2009105508 A2 | 8/2009 |
| WO | WO-2009146164 A1 | 12/2009 |
| WO | WO-2010019988 A1 | 2/2010 |
| WO | WO-2010056052 A2 | 5/2010 |
| WO | WO-2010083393 A2 | 7/2010 |
| WO | WO-2010097214 A1 | 9/2010 |
| WO | WO-2011034780 A1 | 3/2011 |
| WO | WO-2011034781 A2 | 3/2011 |
| WO | WO-2011087794 A1 | 7/2011 |
| WO | WO-2011162730 A2 | 12/2011 |
| WO | WO-2012018716 A2 | 2/2012 |
| WO | WO-2012108628 A2 | 8/2012 |
| WO | WO-2012117025 A1 | 9/2012 |
| WO | WO-2012126475 A1 | 9/2012 |
| WO | WO-2012150843 A2 | 11/2012 |
| WO | WO-2012158769 A1 | 11/2012 |
| WO | WO-2015028157 A1 | 3/2015 |

OTHER PUBLICATIONS

"European Application Serial No. 13182321.3, European Search Report dated Nov. 6, 2013", 3 pgs.

"International Application Serial No. PCT/EP2014/050476, International Preliminary Report on Patentability dated Mar. 1, 2016", 5 pgs.

"International Application Serial No. PCT/EP2014/050476, International Search Report dated Feb. 25, 2014", 4 pgs.

"International Application Serial No. PCT/EP2014/050476, Written Opinion dated Feb. 29, 2016", 4 pgs.

"International Registration for Industrial Design DM/066737, registered Dec. 28, 2004", 1 pg.

"International Registration for Industrial Design DM/069005, registered May 14, 2007", 1 pg.

"International Registration for Industrial Design DM/075207, registered Jan. 24, 2011", 1 pg.

(56) References Cited

OTHER PUBLICATIONS

"International Registration for Industrial Design DM/076499, registered May 23, 2011", 1 pg.
"International Registration for Industrial Design DM/077057, registered Sep. 9, 2011", 1 pg.

* cited by examiner

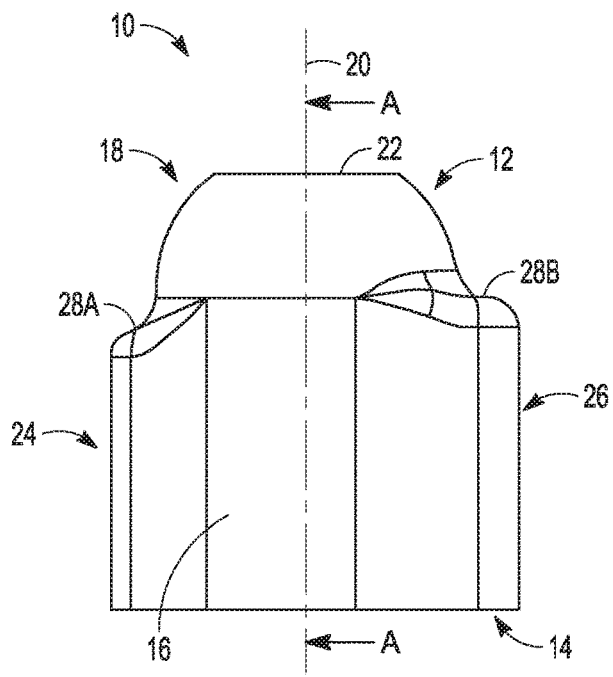
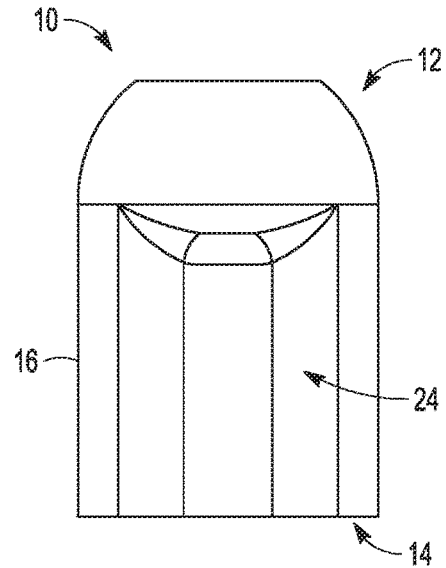
FIG. 1    FIG. 2
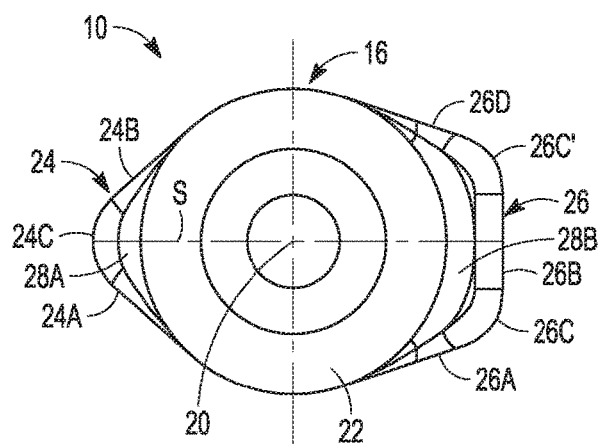
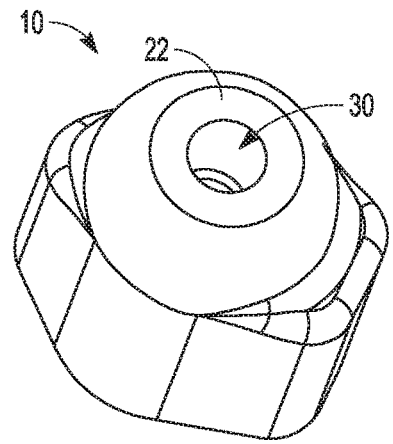
FIG. 3    FIG. 4

INTRAORAL REFERENCE BODY

CLAIM OF PRIORITY

This application is a U.S. National Stage Filing under 35 U.S.C. 371 from International Application No. PCT/EP2014/050476, filed on 13 Jan. 2014, and published as WO 2015/028157 A1 on 5 Mar. 2015, which claims the benefit to European Application No. 13182321.3, filed on 30 Aug. 2013, the benefit of priority of each of which is claimed hereby, and each of which are incorporated by reference herein in its entirety.

The present disclosure relates to a reference body for intraoral scan procedures.

In order to plan prosthetic components of a patient's dentition, virtual three-dimensional models are frequently used. Such models are obtained e.g. by scanning the dentition in situ, i.e. intraorally, using optical scanners. An intraoral scan of the patient's dentition has the advantage that it is not necessary to create a physical model of the dentition based on dental imprints which in turn is scanned by a conventional dental scanner. Hence, intraoral scanning is more cost-effective and yields results faster than conventional techniques.

During an optical intraoral scan process, a rather small optical scanner is moved along a patient's dentition. Images of adjacent portions of the dentition are "stitched" together by a suitable software. The combined image of the dentition can be used to calculate a three-dimensional model of the dentition or selected parts of it. Although this approach yields reliable results in most cases, the position and/or orientation of implants which are almost completely hidden in the bone and/or the gingiva of the patient cannot be detected unambiguously. In other words, the position and/or orientation of implants cannot be determined with the required precision by intraoral scanning. This information, however, is crucial to select a suitable prosthesis to be placed on the implant.

To indicate the position and/or orientation of the implant, a reference body can be provided. Such a reference body is adapted to be releasably mountable to the dental implant during the scan procedure. During scanning, images of the reference body are acquired. From these images, the three-dimensional geometry of the reference body can be derived. Since said geometry is known, an information regarding the spatial orientation of the reference body can be determined that in turn unambiguously indicates the spatial position and/or orientation of the implant. The corresponding data can then be included in the three-dimensional data set representing the patient's dentition allowing to choose the best prosthetic component to be mounted on the implant.

Although the use of a reference body during intraoral scanning is in principle known, there is still a need for reference bodies that are simple to produce and that can be easily mounted to the implant. Moreover, the reference body should be designed such, that its geometry and/or spatial orientation can be detected reliably with minimized computational efforts.

The reference body according to the present disclosure comprises a cylindrical body portion extending along a longitudinal axis from an apical end to a coronal end, the apical end facing, in particular abutting, the dental implant in a mounted state of the reference body. Further, a coronal end surface is provided defining the coronal end of the reference body. A first radial protrusion protrudes from the body portion in a first radial direction and a second radial protrusion protrudes from the body portion in a second radial direction. The first radial protrusion and the second radial protrusion have different cross-sectional shapes in a cross-section perpendicular to the longitudinal axis of the reference body.

In other words, the cylindrical body can be positioned—directly or indirectly—on the dental implant during the intraoral scan. In particular, suitable mechanisms and/or features are provided that ensure that the reference body and the implant are positioned in an unambiguous manner relative to each other. A well-defined relative positioning can e.g. be achieved by providing the components of the reference body and of the implant that serve for coupling them with complementary geometrical features.

It should be noted in this context that the term "cylindrical" should be understood in the broad sense. A cylindrical body may e.g. have a cross-section which is elliptical or polygonal. Thus, a right circular cylinder is only one example of a cylindrical body in the sense of the present disclosure.

It should generally by noted that, in the context of this disclosure, although somewhat simplifying, anatomical directions/orientations are used as follows:

"Apical" shall mean pointing towards the jawbone or gingiva.

"Coronal" shall mean towards the free end of the teeth of the dentition, i.e. a coronal side is opposite the apical side.

"Lingual" shall mean towards the "inner side" or the "center" of the dental arch, and shall be used in connection with the lower jaw and the upper jaw.

"Buccal" shall generally mean towards the outer side of the dental arch.

The different cross-sectional shapes of the first and second radial protrusions allow to determine the spatial orientation and/or position of the reference body and to simplify the "stitching" procedure to combine images of adjacent regions of the reference body. This aspect is of special importance since the individual digital images acquired during intraoral scanning usually cover only a certain part of the reference body. Moreover, with a hand-held scanner the exact spatial orientation of the scanner during the acquisition of the individual images is per se unknown. This means that said images have to be combined to yield a picture of the reference body as a whole. The first and second radial protrusions and their differing design simplify the process of combining the images as they provide a well-define reference orientation and position with respect to each other.

In an embodiment of the reference body according to the present disclosure, a surface of the first radial protrusion and/or a surface of the second radial protrusion comprise at least two planar segments, in particular wherein transitional portions between said planar segments are rounded. Planar segments are relatively easy to manufacture and can be readily sterilized. Providing rounded transitional portions avoids edges that are difficult to clean and/or that might injure the patient's gingiva.

In a further embodiment of the reference body according to the present disclosure, the cross-sectional shape of the first radial protrusion is wedge-shaped. Alternatively or additionally, the cross-sectional shape of the second radial protrusion is trapezoidal.

In another embodiment of the reference body according to the present disclosure, the extension of the first radial protrusion and/or the second radial protrusion in a longitudinal direction is more than 50% of the extension of the body portion in said longitudinal direction, in particular more than 50% of the extension of the reference body in said direction. The extension of one of the first and second radial protrusions in a longitudinal direction may be different, in particular the extension of the first radial protrusion in the longitudinal direction may be smaller than the extension of the second radial protrusion in said longitudinal direction. Different longitudinal extensions of the protrusions further simplify the identification of the orientation and/or the spatial position of the reference body. In particular, the extension of the first radial protrusion in the longitudinal direction is smaller than the extension of the second radial protrusion in said longitudinal direction.

In an embodiment of the reference body according to the present disclosure, transitional portions between a surface of the body portion, a surface of the first radial protrusion, a surface of the second radial protrusion and/or the coronal end surface are rounded.

In yet another embodiment of the reference body according to the present disclosure, the reference body comprises a coronal cap position disposed on the coronal end of the body portion and the coronal end surface is disposed on the coronal cap portion. The coronal cap portion may resemble at least partially a conical or a hemispherical shape, in particular a frusto-conical or frusto-hemispherical shape. A frusto-conical shape or a frusto-hemispherical shape are in this context conical or hemispherical bodies cropped e.g. by a plane. In other words, a frusto-conical shape is to be understood as a surface, e.g. a planar surface which is disposed in particular perpendicular to the longitudinal axis, with a conical transitional surface extending from the circumference of the cylindrical body portion to said surface. A frusto-hemispherical shape is to be understood as a surface, e.g. a planar surface which is disposed in particular perpendicular to the longitudinal axis, with a transitional surface resembling a segment of a hemisphere extending from the circumference of the cylindrical body portion to said surface. Any other rounded transition between said surface and the cylindrical body portion is conceivable.

The coronal cap portion may comprise a planar coronal surface. In particular said planar surface is disposed in a plane perpendicular to the longitudinal axis of the reference body.

In an embodiment of the reference body according to the present disclosure, the reference body comprises a bore that extends from the coronal end surface into the reference body. In particular said bore extends through the reference body. The bore may in particular be coaxial with the longitudinal axis and/or centric with respect to the body portion of the reference body.

In yet another embodiment of the reference body according to the present disclosure, the body portion comprises a cavity having an opening in an apical surface of the apical end, wherein the cavity is adapted to receive a fastening component to mount the reference body to the implant. E.g. the fastening component is a protrusion projecting from the implant and having a geometry that allows to reliably mount the reference body in an unambiguous orientation to the implant. The apical interface formed by the cavity may be specific to a given implant type.

The coronal end surface may comprise a rim surrounding the bore, e.g. to indicate a specific property of the implant and/or the reference body, e.g. the implant type with which the reference body is intended to be used.

In an embodiment of the reference body according to the present disclosure, the bore comprises a step portion having an enlarged diameter at a coronal end portion of the bore. Said step portion may indicate certain properties of the implant and/or the reference body, e.g. its size.

The bore and the cavity may be connected forming a passage from the coronal end surface to the apical end of the body portion. Said passage may e.g. be provided to allow introducing a fastener, such as a screw, to mount the reference body reliably to the implant.

In an embodiment of the reference body according to the present disclosure, the body portion comprises a segment that is in a circumferential direction free of protrusions, in particular wherein said segment is formed on the apical end of the body portion. Said segment is disposed in or close to the apical end of the body portion. Especially in cases where the reference body has to be mounted to a relatively deep seating implant, such an embodiment facilitates the mounting procedure.

In particular, the first radial protrusion may be disposed on the lingual side in a mounted state of the reference body. The second radial protrusion may be disposed on the buccal side in a mounted state of the reference body.

The features and embodiments described above may be readily combined with each other.

More areas for applicability of the present invention will become apparent from the detailed description provided hereinafter. It should be understood that the detailed description and specific examples are intended for the purpose of illustration only and are not intended to limit the scope of the invention in any way. The Figures are simplified and schematic. Details not necessary for the understanding for the invention are omitted.

The present disclosure will be explained in more detail and become fully understood from the detailed description and the accompanying drawings.

Figure 12:
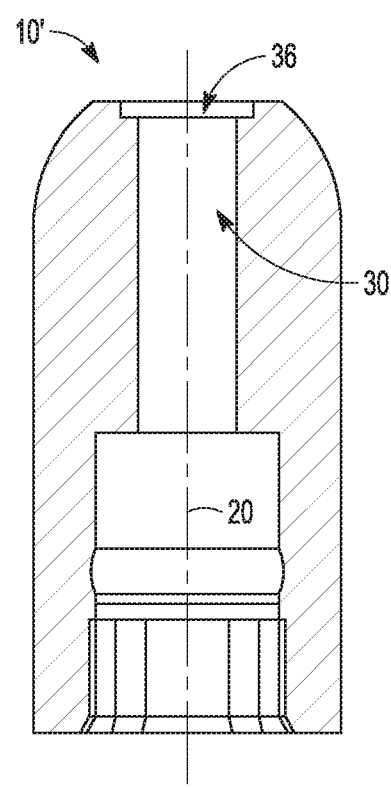
Figure 13:
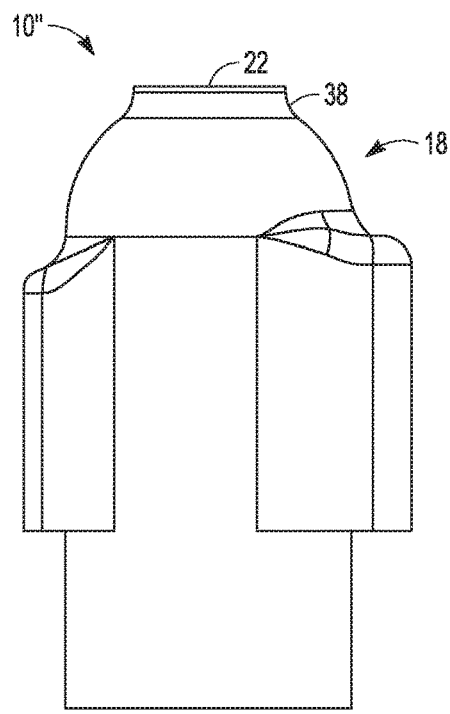
Figure 14:
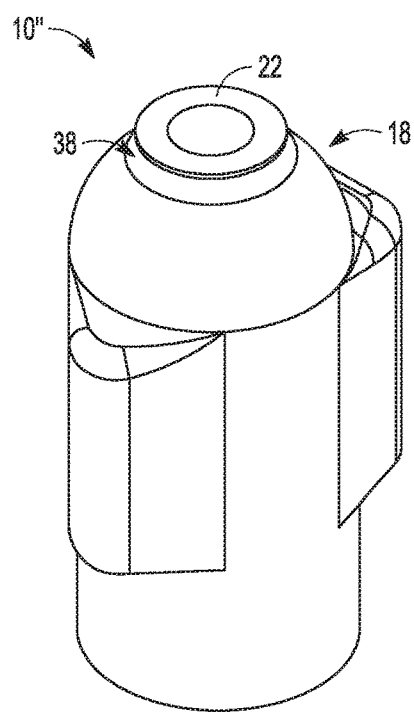

FIGS. 1 to 6 show different views of a first embodiment of the reference body according to the present disclosure, FIGS. 7 to 12 show different views of a second embodiment of the reference body according to the present disclosure, and FIGS. 13 and 14 show two views of a third embodiment of the reference body according to the present disclosure.

FIGS. 1 to 6 show a first embodiment 10 of the reference body according to the present disclosure. FIG. 1 shows a side view of reference body 10. It can be seen that reference body 10 comprises a coronal end 12 and an apical end 14. Apical end 14 is suitably designed to allow direct or indirect mounting of body 10 to a dental implant.

Reference body 10 comprises a body portion 16 which is in essence cylindrical. Although body portion 16 has a right circular cylindrical shape, reference bodies with different cross-sectional shapes are also conceivable. The coronal end 12 of body portion 16 is provided with a coronal end surface 18 of frusto-hemispherical shape. Said frusto-hemispherical shape is obtained by cropping a hemisphere by a plane which is in the present case disposed perpendicular to a longitudinal axis 20 of reference body. Thus, coronal end surface 18 comprises a planar coronal surface 22. Planar coronal surface 22 can have other angles than 90° relative to longitudinal axis 20 in other embodiments of the reference body according to the present disclosure.

Body portion 16 is provided with a first radial protrusion 24 and a second radial protrusion 26 which both protrude from the surface of body portion 16 in a radial direction.

FIG. 2 shows a side view in a directional perpendicular to the view of FIG. 1 providing a head-on view on wedge-shaped first radial protrusion 24.

FIG. 3 reveals the shape of protrusions 24, 26 in a top view. First radial protrusion 24 has in essence a wedge shape formed by planar surfaces 24a, 24b connected by rounded transitional portion 24c. In essence, planar surfaces 24a, 24b extend parallel to longitudinal axis 20.

Second radial protrusion 26 is formed by planar surfaces 26a, 26b, 26d connected by transitional portions 26c, 26c'. Planar surfaces 26a, 26b and 26d also extend in essence parallel to longitudinal axis 20. Protrusion 26 is disposed on the opposite side of body portion 16 as protrusion 24. Exemplarily, in a mounted state of reference body 10, the second radial protrusion 26 indicates the buccal side of reference body 10 and first radial protrusion 24 indicates the lingual side.

FIG. 3 further reveals that reference body 10 is symmetric relative to symmetry plane S comprising longitudinal axis 20. In the plane shown in FIG. 3, symmetry plane S intersects the tip of the wedge shape of first radial protrusion 24 and the center of planar surface 26b. Thus, symmetry plane S essentially extends in a mounted state of reference body 10 in a lingual-buccal and apical-coronal direction.

It can be seen from FIG. 1 that the apical ends of protrusions 24, 26 extend to the apical end 14 of body portion 16. In other words, their apical ends are flush with the apical end 14 of body portion 16. The coronal ends of protrusions 24, 26 comprise end surfaces 28a, 28b which are connected with the surface of body portion 16, with the planar surfaces 24a, 24b, 26a, 26b, 26d and with the transitional portions 24c, 26c, 26c' by rounded transitions. These transitions in connection with transitional portions 24c, 26c and 26c' give reference body 10 a "soft" or "organic" appearance that on the one hand facilitates the mounting of reference body 10 to an implant and that on the other hand improves the acceptance of the reference body 10 as patients in many cases dislike sharp edged objects in their mouth.

The different cross-sectional shapes of protrusions 24, 26 allow to identify unambiguously the position and/or orientation of the reference body and thus of the implant to which it is connected. Further, the geometry of the reference body 10 provides enough characteristic features to facilitate a reliable combination of overlapping partial images of reference body 10 which have to be "stitched" together it to provide an image of reference body 10 as a whole.

FIG. 4 depicts an isometric perspective view of reference body 10 showing that planar coronal surface 22 is ring-shaped as a bore 30 extends coaxially to longitudinal axis 20 into reference body 10.

Figure 6:
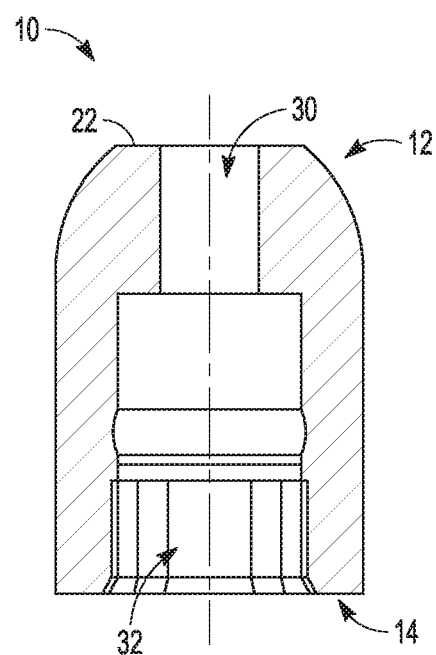
Figure 7:
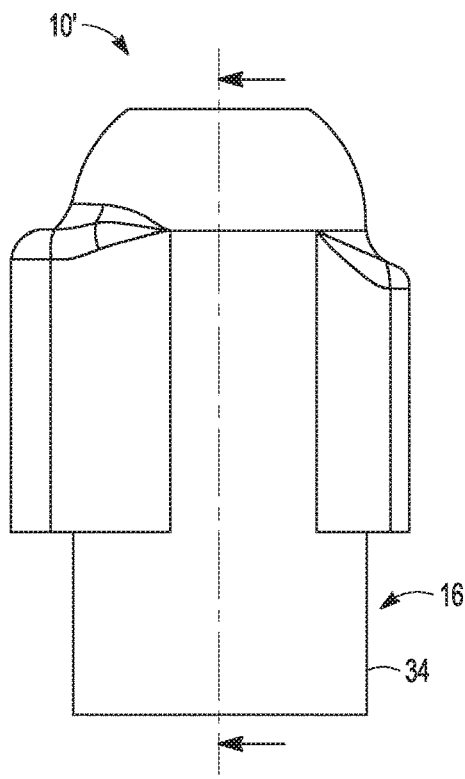
Figure 8:
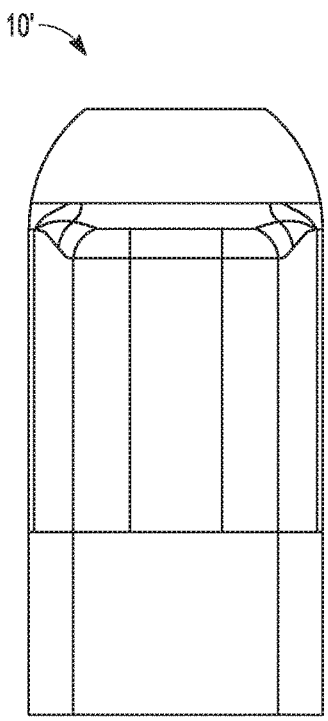

As it can be seen from FIG. 6, which shows a cross-section through reference body 10 along plane A-A indicated in FIG. 2, bore 30 is connected with a cavity 32 which extends from the apical end 14 into reference body 12. Cavity 32 is configured to receive a protrusion projecting from the implant or an intermediate piece provided between the implant and reference body 10 to allow the mounting of reference body 10 to the implant. Cavity 32 may be specifically shaped to allow a tight and/or well-defined fit with a complementary interface on a specific implant. Bore 30 gives access to cavity 32 from the coronal end 12 in order to be able to mount or dismount reference body from the implant. A plethora of different systems for fixing reference body 10 to the implant is conceivable. A connection system comprising threaded members may be provided. Alternative or additionally, a snap fit connection may be provided.

FIG. 5 shows a bottom view of reference body 10 revealing that sidewalls of cavity 32 are designed such, that reference body 10 can only be mounted in a well-defined manner to the implant which is provided with a correspondingly shaped protrusion. To this end, cavity 32 comprises in this exemplarily shown embodiment two essentially planar sidewalls 32a, 32b angled relative to each other and two curved sidewalls 32 which may be provided with different curvature radii.

FIGS. 7 to 12 show a further embodiment 10' of the reference body according to the present disclosure. Reference body 10' has a longer body portion 16 than body portion 16 of reference body 10 and can thus be used e.g. in combination with smaller sized and/or deeper seated implants.

Contrary to reference body 10, reference body 10' is provided with a apical segment 34 which is not provided with protrusions. In particular, protrusions 24, 26 do not extend over segment 34 which is therefore easier to insert into the gingiva of the patient.

Figure 9:
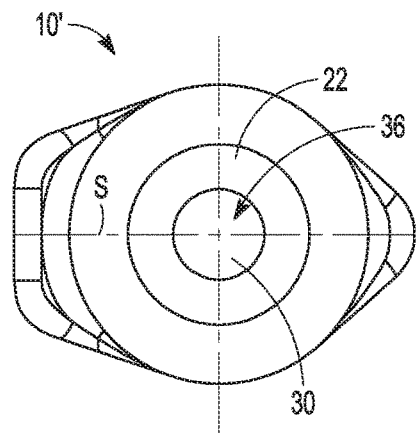
Figure 10:
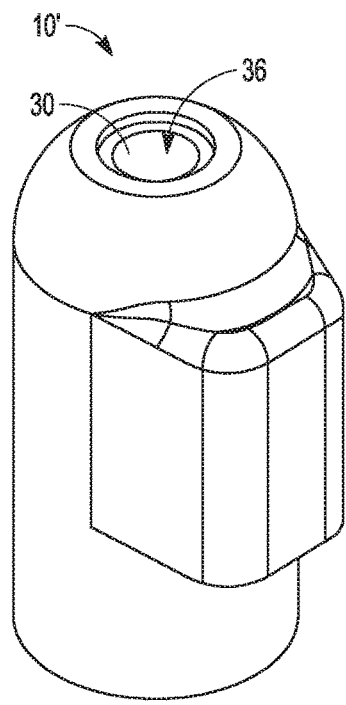
Figure 11:
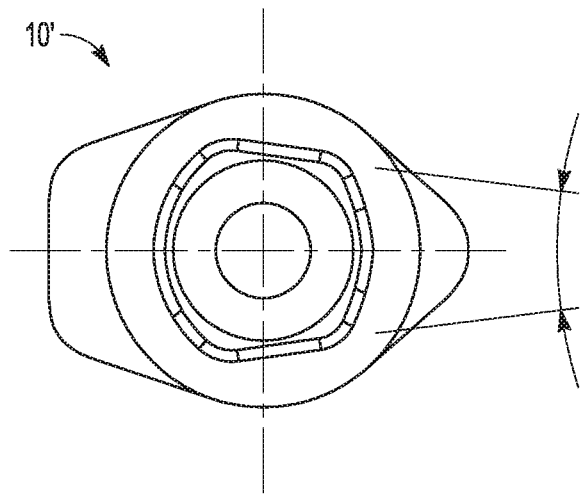

In order to be able to distinguish between reference body 10 and reference body 10'—especially in cases when apical segment 34 is positioned almost entirely in the gingiva of the patient—an coronal end of bore 30 is provided with a stepped portion 36 having a slightly larger diameter than bore 30 itself (cf. e.g. FIGS. 9, 10 and 12). Stepped portion 36 is readily identified during an intraoral scan and it can be automatically or manually determined that a specific reference body is used which in turn indicates the presence of a specific implant. Of course, the dimensions and/or the shape of stepped portion 36 may be used to identify a number of differently sized reference bodies.

An alternative feature that allows distinguishing between different reference bodies is shown in connection with embodiment 10" of the reference body according to the present disclosure. Said embodiment 10" is shown in FIGS. 13 and 14. Coronal end surface 18 of reference body 10" is provided with a rim 38 disposed on the coronal end of frusto-hemispherically shaped portion of coronal end surface 18. The coronal end of rim 38 carries the ring-like coronal surface 22. The shape and/or the dimensions, especially in an axial direction parallel to longitudinal axis 22, may indicate specific characteristics of the reference body and/or the implant.

It should be understood that stepped portion 36 and/or rim 38 can also be provided on reference body 10.

The description is mainly of exemplary nature and, thus, variations that do not depart from the gist of the disclosed teachings are intended to be within the scope of the disclosure.

REFERENCE NUMERAL LIST 10, 10', 10" reference body
12 coronal end
14 apical end
16 body portion
18 coronal end surface
20 longitudinal axis
22 planar coronal surface
24 first radial protrusion
26 second radial protrusion
24a, 24b planar surface
26a, 26b, 26c planar surface
24c, 26c, 26c' transitional portion
28a, 28b end surface
30 bore
32 cavity
32a, 32b, 32c, 32d sidewall
34 apical segment 36 stepped portion
38 rim
AA cross-sectional plane
S symmetry plane

The invention claimed is:

1. A reference body for intraoral scan procedures adapted to be releasably mountable to a dental implant, wherein the reference body comprises:
    a cylindrical body portion, an apical end, and a coronal end, the apical end abutting the dental implant in a mounted state of the reference body, wherein a longitudinal axis extends through the cylindrical body portion and defines a longitudinal direction,
    a coronal end surface defining the coronal end of the reference body,
    a first radial protrusion protruding from the cylindrical body portion in a first radial direction, wherein the first radial protrusion has a coronal end that terminates a distance apically spaced apart from the coronal end of the reference body, and
    a second radial protrusion protruding from the cylindrical body portion in a second radial direction, wherein the first radial protrusion and second radial protrusion have different cross sectional shapes in a cross-section perpendicular to the longitudinal axis, and
    wherein the extension of the first radial protrusion in the longitudinal direction is smaller than the extension of the second radial protrusion in the longitudinal direction, and wherein the first radial protrusion has an apical end that is flush with the apical end of the reference body.

2. The reference body according to claim 1, wherein a surface of at least one of the first radial protrusion and the second radial protrusion comprises at least two planar segments.

3. The reference body according to claim 2, wherein the cross-sectional shape of the first radial protrusion is wedge-shaped.

4. The reference body according to claim 3, wherein the cross-sectional shape of the second radial protrusion is trapezoidal.

5. The reference body according to claim 1, wherein the extension of at least one of the first radial protrusion and the second radial protrusion in the longitudinal direction is more than 50% of the extension of the reference body in the longitudinal direction.

6. The reference body according to claim 1, wherein transitional portions between a surface of the body portion, a surface of the first radial protrusion, a surface of the second radial protrusion and the coronal end surface are rounded.

7. The reference body according to claim 1, wherein the coronal end surface comprises a planar coronal surface disposed in a plane perpendicular to the longitudinal axis of the reference body.

8. The reference body according to claim 1, wherein the reference body comprises a bore that extends from the coronal end surface coaxially to the longitudinal axis through the reference body.

9. The reference body according to claim 8, wherein the coronal end surface comprises a rim surrounding the bore.

10. The reference body according to claim 9, wherein the bore comprises a step portion having an enlarged diameter at a coronal end of the bore.

11. The reference body according to claim 1, wherein the cylindrical body portion comprises a cavity having an opening in an apical surface of the apical end of the reference body, wherein the cavity is adapted to receive a fastening component to mount the reference body to the implant.

12. The reference body according to claim 11, wherein the bore and the cavity are connected forming a passage from the coronal end surface to the apical end of the body portion.

13. The reference body according to claim 1, wherein the cylindrical body portion comprises a segment that is in a circumferential direction free of protrusions, wherein the segment extends from the apical end of the reference body.

14. The reference body according to claim 1, wherein the second radial protrusion has a coronal end that terminates a distance apically spaced apart from the coronal end of the reference body.

15. The reference body according to claim 1, wherein the second radial protrusion has an apical end that is flush with the apical end of the reference body.

16. A reference body for intraoral scan procedures adapted to be releasably mountable to a dental implant, wherein the reference body comprises:
    a body portion, an apical end, and a coronal end, the apical end abutting the dental implant in a mounted state of the reference body, wherein a longitudinal axis extends through the body portion and defines a longitudinal direction,
    a coronal end surface defining the coronal end of the reference body,
    a first radial protrusion protruding from the body portion in a first radial direction, and
    a second radial protrusion protruding from the body portion in a second radial direction, the extension of the first radial protrusion in the longitudinal direction being smaller than the extension of the second radial protrusion in the longitudinal direction, wherein the first radial protrusion and second radial protrusion have different cross-sectional shapes in a cross-section perpendicular to the longitudinal axis of the reference body, and wherein the first and second radial protrusions each has an apical end that is flush with the apical end of the reference body.

17. The reference body according to claim 16, wherein the body portion comprises a segment that is in a circumferential direction free of protrusions, wherein the segment extends from the apical end of the reference body.

18. The reference body according to claim 16, wherein the body portion comprises a cavity having an opening in an apical surface of the apical end, wherein the cavity is adapted to receive a fastening component to mount the reference body to the implant.

19. The reference body according to claim 16, wherein the first and second radial protrusions each has a coronal end that terminates a distance apically spaced apart from the coronal end of the reference body.

* * * * *